United States Patent [19]

Kornacker et al.

[11] Patent Number: 4,832,480
[45] Date of Patent: May 23, 1989

[54] DIFFERENTIAL DIAGNOSIS OF SENSORY ABNORMALITIES USING A NORMALIZED, RATIOMETRIC ANALYSIS OF STEADY STATE EVOKED POTENTIALS

[75] Inventors: Karl Kornacker, Columbus; Marvin E. Monroe, Sunbury, both of Ohio

[73] Assignee: Quintron, Inc., Galena, Ohio

[21] Appl. No.: 157,060

[22] Filed: Feb. 16, 1988

Related U.S. Application Data

[63] Continuation-in-part of Ser. No. 877,855, Jun. 24, 1986, abandoned.

[51] Int. Cl.$^4$ .......................... A61B 5/04; A61B 3/00
[52] U.S. Cl. .................................. 351/246; 351/211; 128/731
[58] Field of Search ....................... 128/76.5, 732, 731; 351/205, 211, 243, 246

[56] References Cited

U.S. PATENT DOCUMENTS 4,181,407 1/1980 Razran ................................ 351/205
4,493,327 1/1985 Bergelson et al. .................. 128/731

Primary Examiner—Rodney B. Bovernick
Assistant Examiner—Jay Patrick Ryan
Attorney, Agent, or Firm—Frank H. Foster

[57] ABSTRACT

A method for testing the visual system to detect the presence of disease, and to distinguish disease which has degraded the linear visual pathway from disease degrading the nonlinear visual pathway in a manner which is substantially independent of the stimulus applied to the eye and the connection of the instrumentation to the patient being tested. Three light sources having their amplitude varied at different frequencies stimulate the eye. The response evoked in the brain is detected and Fourier analyzed. The amplitude of selected Fourier components are detected and used to compute a ratio which removes the dependence upon the factors stated above. The Fourier component amplitude factors are selected so that the number of factors in the numerator of the ratio is equal to the number in the denominator and the sum of the orders of the factors in the numerator are equal to the sum of the orders in the denominator. This provides a ration of the response of the linear system to the response of a nonlinear system, which can be compared to a data bank of such test results to determine whether a particular patient being tested deviates enough from the normal response to suspect disease, and the direction and magnitude of that deviation so that the type and extent of disease can be indicated.

14 Claims, 2 Drawing Sheets

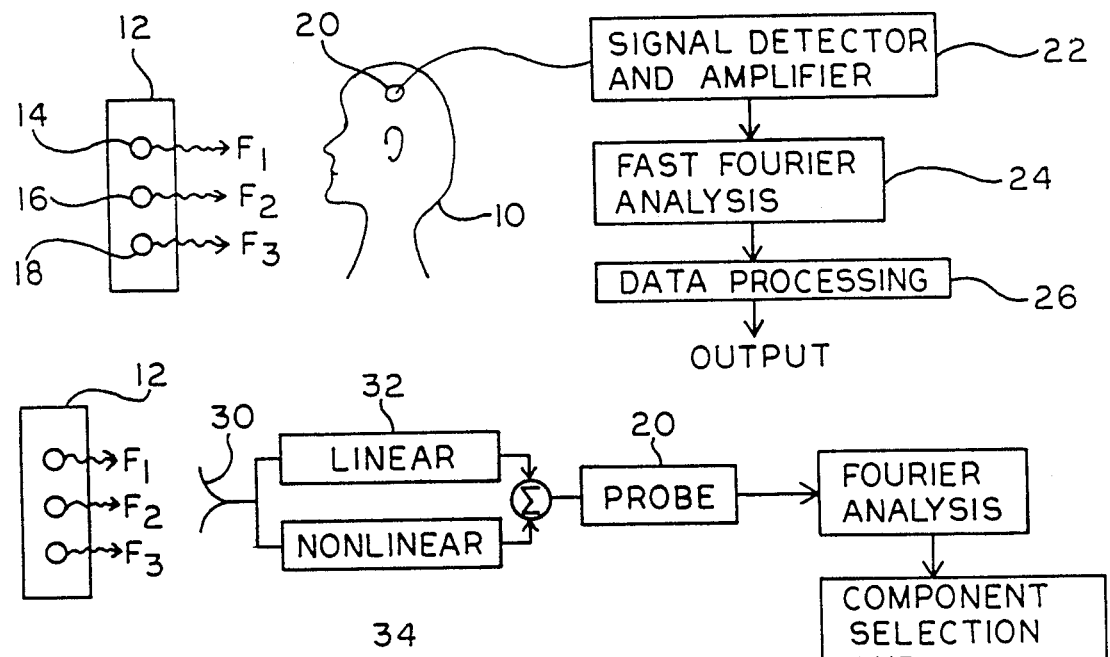
FIG. 1
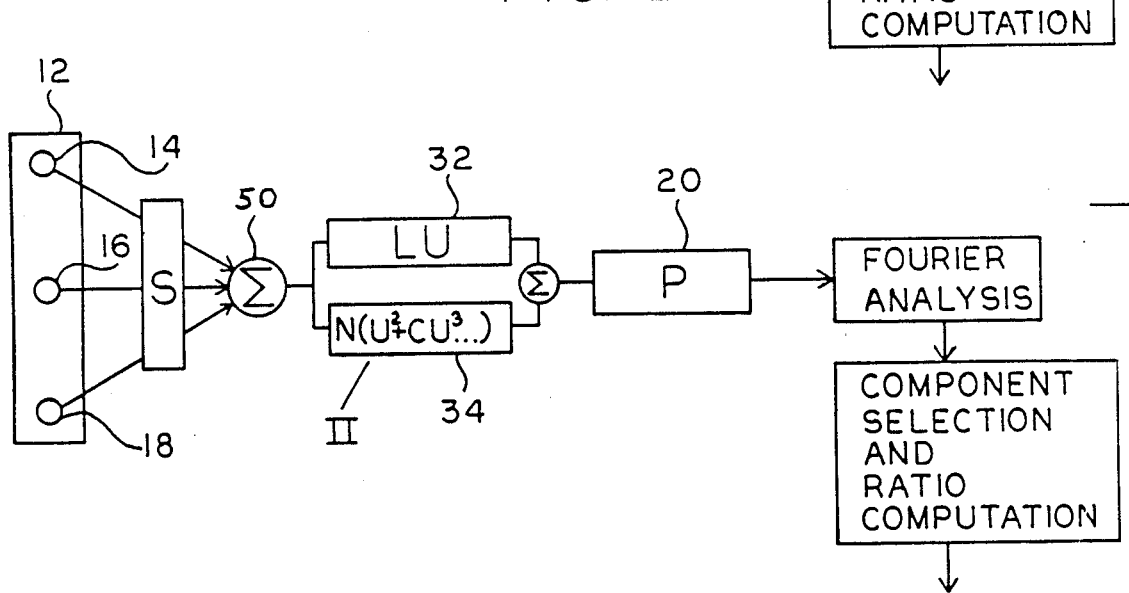
FIG. 2
FIG. 3
$E_0$
$+E \sin W_1 T$
$+E \sin W_2 T$
$+E \sin W_3 T$
$L\ PU(S)$
$+N\ PU^2(S^2)$
$+CN\ PU^3(S^3)$

DIFFERENTIAL DIAGNOSIS OF SENSORY ABNORMALITIES USING A NORMALIZED, RATIOMETRIC ANALYSIS OF STEADY STATE EVOKED POTENTIALS

This is a continuation-in-part of application Ser. No. 877,855, filed on June 24, 1986 now abandoned.

TECHNICAL FIELD

This invention relates generally to medical diagnostic screening tests and more particularly relates to a method for detecting the likelihood of disease of a neurological sensory system, particularly the vision system and when an abnormality is detected for differentiating which of two possible disease conditions is likely.

BACKGROUND ART

Large scale screening of major components of society is a desirable public health tool for the initial detection of possible common disease conditions. For example, periodic testing of the visual system of students for the early detection of glaucoma and other diseases is desirable because early treatment can minimize the extent of damage to the system.

It is desirable that equipment for performing such testing have the capability of being used easily, of performing the test quickly and comfortably, and of providing reliable test results including as much information as possible about a suspected disease in the event of a positive test result.

Many sensory systems of vertebrates, including humans, perform two types of tasks. One type of task is the detection of amplitude or detail information requiring an essentially linear relationship between the input stimulus and the output to the brain. The other, typically involving pattern recognition, requires a strongly nonlinear relationship. Generally, these two types of sensory tasks are carried out by distinct sensory pathways which differ in their susceptibility to various diseases.

For example, the human visual system is composed of two distinct pathways commonly referred to as the X or linear pathway and the Y or nonlinear pathway. The linear pathway, which is responsible for color and acuity vision, originates predominately in the central macula of the human retina. The nonlinear pathway, which detects spatial and temporal patterns, predominates in peripheral vision.

The linear visual pathway originates in small diameter retinal ganglion cells which are highly susceptible to impaired retinal circulation, such as caused by diabetes. Thus, it would be desirable to determine from a test of the human visual system whether there has been degeneration of the linear pathway.

The nonlinear visual pathway originates in large diameter retinal ganglion cells which are highly susceptible to increased intraocular pressure such as is caused by glaucoma. Thus, it would be desirable to detect degeneration of the nonlinear pathway as a result of such a disease condition.

In the past, prior workers have flashed a spot of light on the peripheral retina and also upon the macula, measured transient electrical responses evoked on the scalp and compared those responses. However, this is unsatisfactory because the nonlinear component of the visual response cannot be determined from such measurements. Furthermore, the amplitude measurements are essentially useless for comparing to the amplitude measurements derived from other patients because they are dependent upon the instrumentation itself and the manner in which it is attached to the patient. For example, the amplitude measurements are dependent upon the amount of retinal stimulation and the resistance between the skin and the electrode conventionally used for detecting evoked potentials. Thus, such a system is of little or no value when detecting whether a particular individual suffers from a disease.

Prior workers have applied visual stimulation to the human eye and detected the evoked response. Such systems are disclosed in U.S. Pat. Nos. 3,087,487, 3,172,404, 4,181,407 and 4,493,539. Other patents which test vision or examine evoked responses are U.S. Pat. Nos. 4,293,200, 4,493,327, and 4,462,411.

All of these systems suffer from two major difficulties. First, the test results of each system are also dependent upon (or a function of) the strength of the input visual stimulation signal and the electrical characteristics of the monitoring and recording apparatus. Secondly, these systems are unable to distinguish disease affecting the linear system from disease affecting the nonlinear system when screening a number of different individuals.

It is therefore an object and feature of the present invention to provide a method for testing a neurological sensory system of a vertebrate for disease conditions in a manner which provides normalized test results which are essentially independent of the input signal strengths, anatomical characteristics not being tested, the test equipment and the character of its attachment to the patient being tested.

It is another object and feature of the present invention to provide such a testing system which not only can detect the likelihood of the presence of disease, but additionally can signal the extent of the disease and whether the disease has caused degeneration of the linear pathway or the nonlinear pathway, thus permitting the suspected disease condition to be signalled.

BRIEF DISCLOSURE OF INVENTION

A periodic stimulus is applied to the sensory system of the animal. Preferably this stimulus consists of three different lights directed at the eyes with the amplitude of each being varied at a different frequency. The electrical response to this stimulus which is evoked in the brain is detected and subjected to a fast Fourier transform so that the amplitude of selected Fourier components of the evoked signal may be detected. The particular Fourier component amplitudes which are detected are selected so that they can be used to compute a ratio which represents the ratio of the response of the nonlinear system to the response of the linear system independently of light stimulus amplitude, probe resistance and other anatomical and instrumentation characteristics which are not the subject of the test. In particular, the amplitude factors are selected to provide a ratio such that both the numerator and the denominator of the ratio are the product of a multiplication of Fourier component amplitude factors. The number of factors in the numerator is made equal to the number of factors in the denominator so that the ratio is substantially independent of the resistance of the output path from the human brain to the instrumentation. The sum of the orders of the factors in the numerator is made equal to the sum of the orders of the factors in the denominator so that the resulting ratio is substantially independent of light stimulus amplitude.

By testing a large number of people that are known to have healthy visual systems, a range of healthy ratios can be determined. Thereafter the test result of each patient can be compared to this range not only to determine whether the test result falls outside that range and therefore the particular patient is likely to have a disease condition, but also to indicate whether the disease has affected the linear system or the nonlinear system and the extent of that effect.

BRIEF DESCRIPTION OF DRAWINGS

FIG. 1 is a diagrammatic view illustrating the principal components and steps used in performing the method of the present invention.

FIG. 2 is a block diagram illustrating a technical model for the embodiment of FIG. 1.

FIG. 3 is a block diagram illustrating a simplified mathematical model for the system illustrated in FIG. 2.

Figure 4:
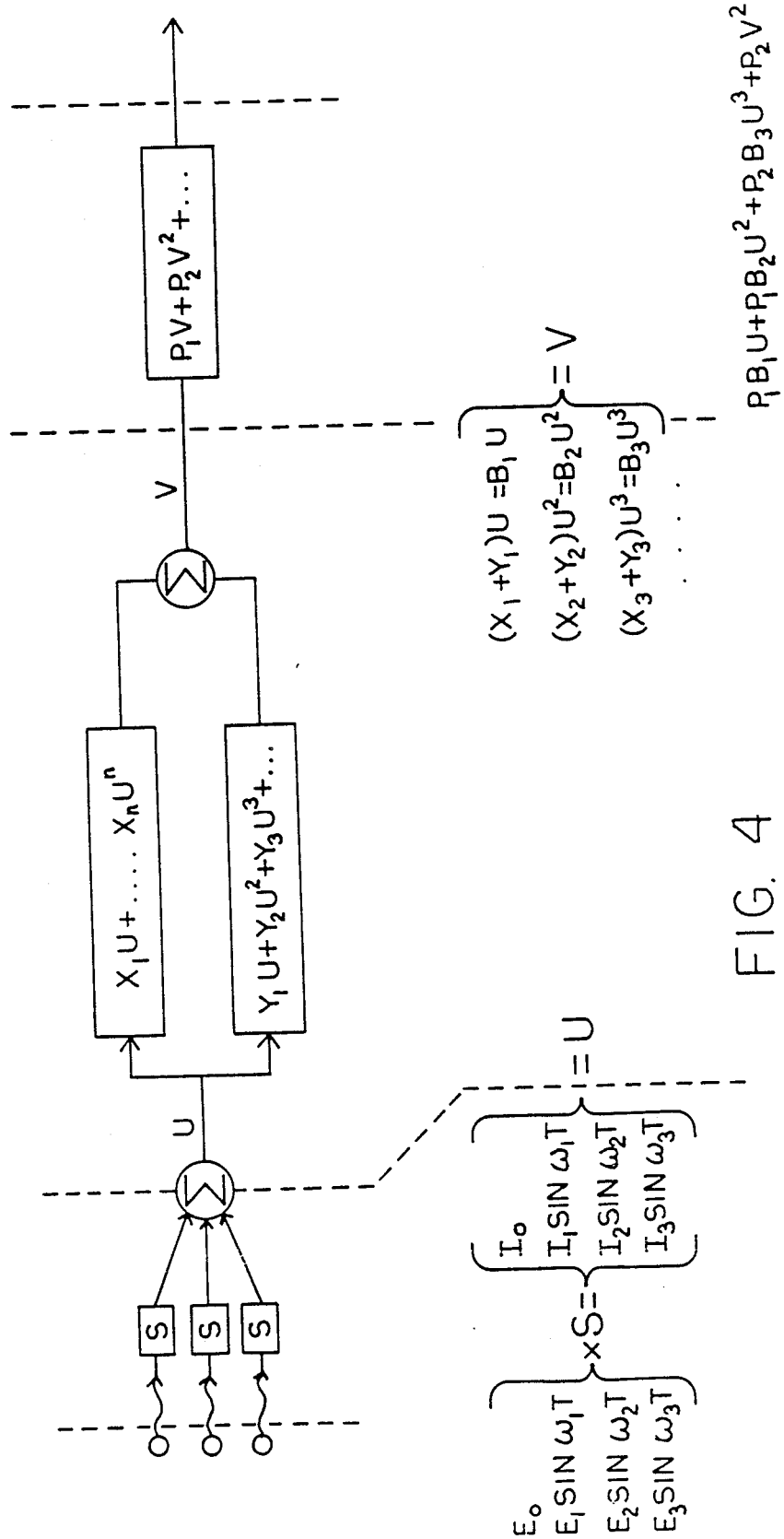
FIG. 4 is a block diagram illustrating a more detailed mathematical model for the embodiment illustrated in FIG. 2.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

Referring to FIG. 1, the eyes of a test subject or patient 10 are stimulated by applying a periodic stimulus 12 to the retina of the subject 10. Preferably, the periodic stimulus 12 consists of three independent light sources 14, 16 and 18, each of which has its light intensity varied at a different frequency f1, f2 and f3. The preferred frequencies are 8Hz, 9Hz and 11Hz and may be obtained by driving each of the lights by a rectangular waveform at a different one of these frequencies.

The stimulation of the visual system, as is well known, evokes electrical activity within the brain of the subject 10. This electrical activity may be detected by conventionally available equipment, such as a surface electrode or probe 20, which is connected to a detector and amplifier 22 which detects the analog signal from the brain. A fast Fourier analysis 24 is then performed in the conventional manner and the results are proessed on conventional data processing equipment 26 in accordance with the principles of the present invention. These results are output to a display or other output device and signal the presence or absence of a disease and the likely type of disease.

FIG. 2 is a model of the system of FIG. 1. It illustrates that the light stimulus 12 applies the light signals to the eye 30 of the subject. Within the retina of the eye 30 the light signals are converted to biological electrochemical signals which travel in the visual sensory system through a separate linear pathway 32 and nonlinear pathway 34 to different portions of the human brain. These biological electrochemical signals generate electrical signals which can be detected by a surface electrode or probe 20 on the scalp of the subject at which the signals from the two pathways are summed.

The purpose of the present invention is to generate a data signal which is substantially directly proportional to the ratio of the gain of the linear path to the gain of the nonlinear path and is substantially independent of the amplitude of the stimulus 12 and the instrumentation. It is particularly desirable that this output data signal be independent of parameters associated with the probe, such as the resistance of the scalp to probe interface which can vary considerably between subjects and is also highly dependent upon the operator and random chance. Of course, either the linear system or the nonlinear system gain can be the numerator and the other can be the denominator to form the desired data signal ratio.

Using this technique, a large number of subjects can be tested to develop a data base. From this data base the normal, average ratio of healthy human beings can be computed along with the standard deviation. Subsequently, individual patients can be tested and their results compared to the data base. The ratio for the particular patient is detected and compared to the normal average ratio for healthy individuals. The standard deviation or other criteria may be used to select a range of values about the average or mean of the ratios stored in the data base. Whenever the ratio for a particular patient being tested falls outside that range, a disease condition is indicated. Furthermore, whether the ratio of a particular patient falls above or below that range determines whether the linear pathway or the nonlinear pathway has degenerated and therefore may be diseased. The extent of the deviation from normal indicates the extent of the disease. Using conventional computer techniques the data indicating whether the ratio for a particular patient is above, within or below the range can be used to generate a variety of messages such as that there exists a 90 percent chance that this particular patient suffers from glaucoma.

FIG. 3 illustrates a mathematical model of the biological system diagrammed in FIG. 2. The signal detected by the probe 20 represents the combination of signals which pass through the linear system 32 as well as those signals which pass through the nonlinear system 34. The light from the three individual sources 14, 16 and 18 must pass through the atmosphere and through the eye tissues and vitreous into the retina where they are summed. This summation is represented as a summing junction 50. Since the light stimulus 12 may be positioned at differing distances from different human subjects during different tests and the light transmission characteristics of the eyes of various subjects may differ, the light path to within the retina may be designated by a gain factor S. This gain factor S effects the intensity of light signals which are received and summed within the retina and is a factor from which the output ratio data signal should be independent.

These three light signals may be represented, as illustrated in FIG. 3, by four signals which are EO representing a DC light level and three sinusoidally varying signals at the three different frequencies f1, f2 and f3. The summation of these signals is designated as U. However, the DC signal EO will not be considered further in this model since it will later be ignored in the Fourier analysis because no DC Fourier components will be selected.

As a result, the summation of the light signals at the beginning of the biological sensory system may be represented as a series, U(S), which is a function of S. Each term of the series U(S) is in the form:

$$SK_m \sin w_m t \qquad \text{I.}$$

where $K_m$ is a different constant for each term $w_m$ represents f1, or f2, or f3 in radians.

In forming the mathematical model illustrated in FIG. 3, certain approximating assumptions are made which are based upon observations by others of the operation of the linear and nonlinear biological pathways. The first assumption is that, for a healthy visual system, all linear terms which are detected by the probe 20 represent signals which were coupled through only the linear pathway of the biological sensory system, and all nonlinear terms which are detected by the probe 20 represent signals coupled through only the nonlinear pathway 34 of the biological sensory system. This approximation is valid because, for a healthy visual system, any nonlinear terms arising in the linear path are negligible as compared to the nonlinear terms arising from the nonlinear path and similarly, any linear terms from the nonlinear path are negligible as compared to the linear terms arising from the linear path.

As a result and ignoring phase shifts, the linear path can be assumed to have a transfer function which is a simple gain factor L so that the output from the linear path 32 is simply LU(S).

The second approximating assumption is that the nonlinear system, if diseased, will degenerate proportionally for all nonlinear terms. Therefore, based upon the first and second assumptions, the transfer function of the nonlinear path, ignoring phase, may be represented as a simple gain factor N with respect to quadratic terms and the product N×C, where C is a proportionality constant, for third order terms. Higher order terms would also have a constant, but since these are not selected or utilized in the preferred embodiment of the present invention, they are not depicted in FIG. 3 and not referred to in the remaining discussion. This is also justified because higher order terms tend to be of smaller amplitude. Thus, the output of the nonlinear biological sensory pathway can be designated by the series:

$$N(U^2 + CU^3 + \ldots) \qquad \text{II.}$$

The third simplifying assumption is that the probe 20 introduces no nonlinearities. Therefore, it may be represented as a gain factor P.

As stated above, U(S) is a series, each term of which is in the form of Equation I. Similarly, applying the principles of Fourier analysis when U(S) is squared, a series of signals will be developed at the output of the nonlinear pathway 34 as $U^2(S^2)$ each term of which is in the form:

$$S^2 K_n \sin w_n t \qquad \text{III.}$$

where $K_n$ is a constant $w_n$ is a second harmonic of f1 or f2 or f3 or a sum or difference of two of those fundamental frequencies.

When U(S) is cubed it will be a function of $S^3$ so that the cubing of U will generate a series $U^3(S^3)$, each term of which is in the form:

$$S^3 K_o \sin w_o t \qquad \text{IV.}$$

where $K_o$ is a constant $w_o$ is f1 or f2 or f3, or a third harmonic, or a sum or difference of f1, or f2 or f3 with a second harmonic, or a sum or difference of all three fundamental frequencies.

The portion of the output signal from the probe 20 which passed through the linear pathway 32 and which is to be applied to the Fourier analysis circuitry will be a series, all the terms of which have the form:

$$LPSK_m \sin w_m t \qquad \text{V.}$$

All the second order terms at the output of the probe 20 are derived from the nonlinear system 34 and will be represented by a series, each term of which is in the form:

$$NPS^2 K_n \sin w_n t \qquad \text{VI.}$$

All the third order terms at the output of the probe 20 which were also derived from the nonlinear path can be represented by a series, all the terms of which will be in the form:

$$NCPS^3 K_o \sin w_o t \qquad \text{VII.}$$

As stated above, the purpose of the invention is to generate a data signal which is both independent of P and S and changes as a result of degeneration of the linear and nonlinear pathways and, furthermore, changes in a manner which indicates which pathway has degenerated and is therefore diseased.

As is well known, a Fourier analysis performing circuit is capable of detecting the amplitude coefficients or amplitude factors of selected sinusoidal signal functions in the form of the series terms V, VI and VII. In the present invention those coefficients are selected, detected by a Fourier transform and formed into a ratio in a manner which cancels the P and S terms and leaves a ratio which is directly proportional to either L or N and inversely proportional to the other.

Each coefficient of the series terms V, VI and VII is a linear function of P; that is each coefficient contains P to the power of 1. Therefore, by making the number of factors in the numerator of the ratio equal to the number of factors in the denominator, P will cancel out.

In addition, each of the coefficients includes a power of S equal to its order. Term V is a first order term and carries S to the power of 1. Term II is a second order term, resulting from squaring of U(S) and therefore carries S to the power of 2. Term VII is a third order term resulting from the cubing of U(S) and therefore carries S to the power of 3. If the sum of the powers or orders of the terms are the same in the numerator as in the denominator, S will also be cancelled out of the ratio.

In addition to the above criteria there must be one, and can only be one, first order or linear factor in the ratio. It may appear in either the numerator or the denominator since a ratio is being developed. The linear term carries information regarding the relative transfer function of the linear pathway. While either the numerator or the denominator must include a linear term, the other must include a non-linear term which represents the relative transfer function of the non-linear pathway.

If one were interested in obtaining the simple transfer function ratio between the linear pathway and non-linear pathway, and was not concerned about cancellation of errors due to the input and output gain factors which can be cancelled as described above, the ratio could include only those two terms. It is preferred, however, to cancel out all of the gain factors in the manner described above.

A further selection criteria is that no higher order or non-linear amplitude factor or Fourier term may be selected for a frequency which is present in the periodic stimulus which is applied to the sensory system. Thus, in selecting the amplitude factors to form the desired ratio, higher order components at frequencies which are present in the periodic stimulus are excluded.

Many differing combinations of terms from the series represented by terms V, VI and VII may be selected in accordance with these principles and can be utilized in the present invention. However, it is desirable to choose lower order terms because the higher order terms generally are of lesser amplitude and are more likely to be at or near harmonic frequencies and thus more difficult to detect or subject to error.

For example, a denominator using a first and fifth order term can be used with a numerator using a second and fourth order term, or alternatively with a numerator using two third order terms. A denominator using a first and sixth order term can be used with a numerator having a second and fifth order term, or alternatively with a numerator having a third and fourth order term. As another example, a numerator using a second and third order term can use a denominator having a first and fourth order term. Of course, the numerators and denominators may be reversed to provide a ratio which may be used.

The preferred ratio may be formed by selecting, detecting and squaring a second order coefficient or amplitude factor and using that as the numerator or denominator of the ratio and also forming the other part of the ratio by selecting, detecting and forming the product of a first order coefficient and a third order coefficient as follows:

$$\frac{(NPS^2 K_n)^2}{(LPSK_m)(NCPS^3 K_o)} \qquad \text{VIII.}$$

The above ratio thus can be reduced to the simple ratio:

$$\left[\frac{K_n}{K_m K_o C}\right] \times \left[\frac{N}{L}\right] \qquad \text{IX.}$$

Since all the K terms and C are constants, the resulting ratio is simply:

$$K\frac{N}{L} \qquad \text{X.}$$

which is directly proportional to a constant and N and inversely proportional to L and thus is wholly independent of P and S.

Therefore, in summary, the desired ratio is preferably represented by the ratio of a second order term squared to the product of a first order term and a third order term.

Although the output of the probe provides many first order, many second order, many third order and many higher order coefficients, judicious selection of both the input frequencies and those output frequencies having coefficients which will be used to develop the ratio of VIII and IX will provide some additional advantages.

The fundamental frequencies, which are the frequencies of the light stimulus 12, are preferably chosen so that:

$$f1 < f2 < 2*f1 \qquad \text{XI.}$$

$$f1 > 2*(f3 - f2) \qquad \text{XII.}$$

The constraints of relation XI are desirable so that all frequencies which are chosen will be below the lowest second harmonic. The reason is that the original sources may not be perfectly linear and therefore may also direct light to the retina at harmonic frequencies. It would be impossible to tell whether Fourier terms at the harmonic frequencies arose within the nonlinear sensory system or arose from the light sources. It will thus be desirable to filter out and avoid all frequencies at or above the lowest second harmonic.

In addition, relation XII permits difference frequencies to be generated which are below f1 and thus can be more easily separated from the fundamental frequencies and could only be generated by the linear system since distortion in sources does not readily produce frequencies below the fundamental.

In the preferred embodiment we have chosen the fundamental frequencies of 8Hz, 9Hz and 11Hz. The steady state response of the eye exhibits a peak in the 8Hz-11Hz range.

Utilizing these fundamental frequencies and applying the Fourier analysis, many second order terms are generated including those at 1Hz, 2Hz and 3Hz. It is preferred to select one of these to obtain the desired ratio because they are substantially below the lowest fundamental frequency and therefore easily separated from it.

Also, using these frequencies a number of third order frequency terms are also generated, including those at 5Hz, 6Hz, 7Hz, 10Hz, 12Hz, 13Hz and 14Hz. We prefer to select the coefficient of the sinusoidal signal at 6Hz because it is outside and below the range of the fundamentals, is formed by a relationship using all three frequencies and cannot arise through any nonlinearity of the source.

By choosing the Fourier coefficients in accordance with the above principles and by forming the ratio described above, a ratio is formed which is directly proportional to degradation of one pathway and inversely proportional to degradation of the other. By choosing three sources, we are able to choose Fourier coefficients for forming this ratio which will not be subject to errors which arise from nonlinear light sources, if sources 14, 16 and 18 are nonlinear. When three sources are used, even if they are non-linear, they can not interact to produce a stimulus which includes frequencies at sums and differences of their respective signals. They only produce harmonics of their fundamentals. Thus, sum and difference frequencies can be selected and detected to form the desired ratio and still meet all the selection criteria.

However, the present invention may, under special circumstances, also be utilized with one or two sources. If a single source is used, all the outputs from the probe will be harmonics of the single source. Therefore, the first, second and third order terms will all be amplitude coefficients of these harmonics. If the single source is perfectly linear, the amplitude coefficient of each higher second order or third order harmonic would arise solely from the activity of the nonlinear pathway and therefore the present invention would work. However, if the single source were nonlinear, then the amplitude coefficients which were detected by the Fourier analysis would arise in part from the nonlinear system and in part from the nonlinearity of the source. This would result in error and therefore the single source would not work if it had substantial nonlinearity.

Two sources can also be used if they are driven by perfect square waves because a perfect square wave has no second order harmonic content, only odd harmonics. Thus, the coefficient of a second harmonic in the output could be selected and utilized in forming the ratio.

However, it is still preferred to use three sources because this allows coefficients to be used at frequencies, none of which are harmonics or sum and difference frequencies centered about harmonics.

Finally, it is also possible to use a single linear source and drive it with a signal having three different frequencies present, f1, f2 and f3 in the drive signal so that all three frequencies are directed at the retina from a single source. However, this too requires a substantially linear source in order to avoid the introduction of harmonics and thus is also not preferred.

As a result of the present invention a method for detecting disease can be performed which is not subjective but rather provides a quantitative output, the value of which is indicative of the extent of the disease. Furthermore, the value of the output indicates which pathway is diseased and therefore which type of disease condition is likely to exist. The test of the present invention also does not require a voluntary response from the human subject being tested and therefore can be utilized with a comatose person and other animals.

FIG. 4 shows a mathematical model, similar to that of FIG. 3 but with fewer simplifying assumptions. It may be used for a more vigorous analysis in accordance with the above described principles.

The method of the present invention may be applied by analogy to any other sensory systems which may be found by medical science to have linear and non-linear pathways which can be anatomically or physiologically isolated as separate pathways and therefore subject to separate disease. For example, instead of three separate light sources, the stimulus could be three separate audio speakers which are energized by the electronically analogous signals, such as those which drive the light stimuli of FIG. 1. Frequencies which are used would be different from those used for the visual system. Frequencies would be used which are near or within the normal hearing range of the particular vertebrate being tested.

Similarly, electro-mechanical transducers which are conventionally available for converting electrical signals to mechanical vibrations might be used to apply sensory stimuli to the skin or other sensory nerves of a vertebrate.

While certain preferred embodiments of the present invention have been disclosed in detail, it is to be understood that various modifications may be adopted without departing from the spirit of the invention or scope of the following claims.

We claim:

1. A machine implemented method for testing a visual sensory system of a vertebrate to obtain measurements for use in determining whether a disease condition exists and for differentiating disease affecting the linear pathway of the sensory system from disease affecting the non-linear pathway of the sensory system, the method comprising:
   (a) applying a periodic visual stimulus to the eye of the vertebrate;
   (b) detecting the periodic electrical signal evoked by the stimulus in the brain of the vertebrate;
   (c) detecting the amplitude of selected Fourier components of the evoked signal, said components being selected to enable the performance of step (d) and to exclude any higher order components at frequencies which are present in said periodic visual stimulus, one of said components being a first order factor;
   (d) machine computing a ratio having a numerator and a denominator representing the ratio of the transfer functions of said linear and non-linear pathways, either the numerator or denominator including a first order amplitude factor selected and detected in step (c) and the other including a higher order amplitude factor selected and detected in step (c).

2. A method in accordance with claim 2 wherein the numerator and the denominator are each a product of a multiplication of selected Fourier component amplitude factors, the number of factors in the numerator being equal to the number of factors in the denominator so that output gain factors will be cancelled and the sum of the orders of the factors in the numerator being equal to the sum of the orders of the factors in the denominator so that input gain factors will be cancelled.

3. A method in accordance with claim 2 further comprising:
   (e) applying the method of claim 1 to a base of vertebrates of like species to detect and store a data base of said ratios;
   (f) selecting a range of values of said ratio about the average or mean of the ratios of the data base; and
   (g) machine computing the ratio from a test of a particular vertebrate signalling whether the ratio is within the range.

4. A method in accordance with claim 3 and further comprising machine computing the amount by which the ratio falls outside said range.

5. A method in accordance with claim 4 wherein the stimulus comprises a radiating light source.

6. A method in accordance with claim 5 wherein said periodic visual stimulus comprises three light sources, each source having its light intensity varied at a different frequency.

7. A method in accordance with claim 6 wherein the frequency of each source is less than the second harmonic of the lowest source frequency.

8. A method in accordance with claim 7 wherein the source frequencies are selected so that the lowest source frequency is greater than twice the difference between the other two frequencies.

9. A method in accordance with claim 8 wherein the frequencies are 8, 9 and 11Hz.

10. A method in accordance with claim 7 wherein each selected Fourier amplitude factor is a coefficient of a Fourier term below the second harmonic of the lowest source frequency.

11. A method in accordance with claim 1 or claim 2 wherein said periodic visual stimulus comprises three light sources, each source having its light intensity varied at a different frequency and wherein one of either said numerator or said denominator is the squared amplitude of a second order factor and the other of said numerator or said denominator is the product of the amplitude of a first order factor and the amplitude of a third order factor.

12. A method in accordance with claim 1 or 2 or 3 wherein said periodic stimulus is a single linear light source driven by a sinusoidal signal.

13. A method in accordance with claim 1 or 2 or 3 wherein said periodic stimulus is a single linear light source driven by a signal having Fourier components of at least three different frequencies.

14. A method in accordance with claim 1 or 2 or 3 wherein said periodic stimulus is two light sources driven by square wave signals at two different frequencies.

* * * * *